United States Patent [19]

Townend et al.

[11] 4,083,857

[45] Apr. 11, 1978

[54] PROCESS

[75] Inventors: John Townend, Madeley Heath, near Crewe; Richard Hazard, Cropston, both of England

[73] Assignee: Fisons Limited, London, England

[21] Appl. No.: 672,275

[22] Filed: Mar. 31, 1976

[30] Foreign Application Priority Data

Apr. 11, 1975 United Kingdom ............... 14913/75

[51] Int. Cl.$^2$ .......................................... C07D 311/16
[52] U.S. Cl. .............................................. 260/343.44
[58] Field of Search ..................... 260/343.2 R, 343.44

[56] References Cited

U.S. PATENT DOCUMENTS 3,665,013 5/1972 Fitzmaurice et al. ......... 260/343.2 R

OTHER PUBLICATIONS

Gore In: Olah, Friedel–Crafts and Related Reactions, vol. IV, Part I, Acylation and Related Reactions, p. 46, (1964).

Primary Examiner—Natalie Trousof
Assistant Examiner—Jane T. Fan
Attorney, Agent, or Firm—Merriam, Marshall & Bicknell

[57] ABSTRACT

There is provided a process for the preparation of coumarin derivatives of the formula:

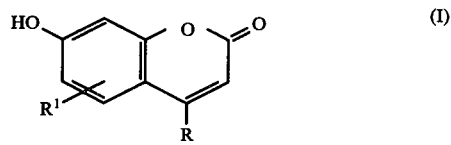

(I)

(wherein R represents substituted or unsubstituted alkyl, aryl or aralkyl, $R^1$ represents alkanoyl, and the hydroxy and $R^1$ substituents are ortho to one another) in which a hydroxy-substituted coumarin of the formula:

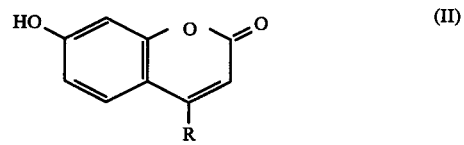

(II)

is acylated in the presence of a Friedel-Crafts catalyst. The compounds of formula I are intermediates in the preparation of certain pharmaceutically-active chromones.

9 Claims, No Drawings

PROCESS

This invention concerns processes for the preparation of coumarin derivatives.

In one aspect, this invention provides a process for the preparation of coumarin derivatives of the formula:

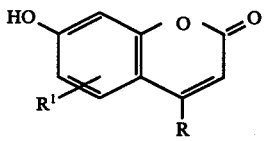

(wherein R represents a substituted or unsubstituted alkyl, aryl, or aralkyl group, $R^1$ represents an alkanoyl group, and the hydroxy and $R^1$ substituents are ortho to one another) in which a hydroxy-substituted coumarin of the formula:

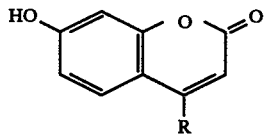

(wherein R is as defined hereinbefore) is acylated in the presence of a Friedel-Crafts catalyst to give the desired compound of general formula I.

R preferably represents an unsubstituted alkyl group having from 1 to 4 carbon atoms, an especially preferred such group being methyl.

The acylation agent employed should naturally be chosen appropriately so as to give the desired group $R^1$ in the compound of formula I produced, preferred groups $R^1$ being alkanoyl groups having from 1 to 6 carbon atoms, especially acetyl. Preferred acylation agents are those of the formula $R^1COX$ (where $R^1$ is as defined hereinbefore and X represents chlorine, bromine, hydroxy or $-OOCR^1$ (where $R^1$ is as defined hereinbefore), thus acyl chlorides and bromides, carboxylic acids and carboxylic acid anhydrides. The preferred agents for producing a compound of formula I wherein $R^1$ represents acetyl are thus acetyl chloride, acetyl bromide, acetic acid or acetic anhydride, acetyl chloride being the most preferred.

The Friedel-Crafts catalyst employed is conveniently aluminum chloride, but other Lewis acids, for example zinc chloride or ferric chloride, may alternatively be employed. If desired, a melt characteristic modifier, for example sodium chloride, which is inert under the reaction conditions may be incorporated into the reaction mixture.

The molar ratio of Friedel-Crafts catalyst to hydroxy-substituted coumarin of general formula II is preferably from 3.8:1 to 6.0:1, and the molar ratio of melt characteristic modifier to Friedel-Crafts catalyst is preferably from 1:1 to 0.1:1. Conveniently, from 1.0 to 1.2 moles of acylation agent are employed per mole of hydroxy-substituted coumarin of general formula II.

The reaction is desirably carried out at a temperature of from 130° to 200° C, and more preferably at a temperature of from 140° to 170° C.

Naturally, this invention extends to a coumarin derivative of general formula I, whenever prepared by a process as described herein.

The coumarin derivatives of general formula I are useful as intermediates in the preparation of pharmacologically active compounds described and claimed in the complete specification of our U.S. Pat. No. 3,419,578 issued Dec. 31, 1968. In particular, 4-methyl-7-hydroxy-8-acetylcoumarin may be converted to 2,6-dihydroxyacetophenone by hydrolysis with an aqueous solution of an alkali-metal base, e.g. sodium hydroxide.

Hitherto, the compounds of general formula I have been prepared by a process involving a Fries rearrangement. Such a reaction commercially involves complex apparatus, which is obviated by the process of the present invention. Moreover, we have found that the yield obtainable in the present process is surprisingly higher than that obtainable in the process involving the Fries rearrangement.

The invention will now be further described, though only by way of illustration, in the following Example.

EXAMPLE

4-Methyl-7-hydroxy-coumarin (26.4g), aluminum chloride (76.1g) and sodium chloride (9.5g) were placed in a flask and shaken to effect reasonable mixing. The flask was then immersed in an oil bath, and the temperature raised to 150° C. Hydrogen chloride evolution commenced at about 100°–110° C. After maintaining the temperature at 150° C for 15 minutes, the melt produced was heated to 160° C and stirred until evolution of hydrogen chloride ceased. Stirring was continued while acetyl chloride (11.8 ml) was added to the melt over a period of about 30 minutes. After maintaining the melt at 160° to 165° C for a further 15 minutes, it was poured with stirring into water (1000 ml). The solid produced was filtered off, washed free of chloride, and dried. On analysis, it was found that the solid contained about 70% by weight of 4-methyl-7-hydroxy-8-acetyl-coumarin and about 30% by weight of 4-methyl-7-hydroxy-6-acetyl-coumarin. The latter isomer was removed by recrystallisation of the product three times from 85% IMS to yield 20.4g of a 4-methyl-7-hydroxy-8-acetyl-coumarin, mpt 167°–169° C.

We claim:

1. A process which comprises reacting a hydroxy-substituted coumarin of the formula

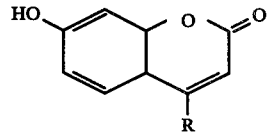

with an acylating agent containing an alkanoyl group in the presence of a Friedel-Crafts catalyst to produce a coumarin derivative of the formula

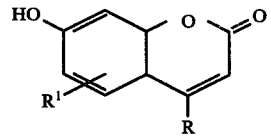

wherein the formulas R represents an unsubstituted alkyl group, $R^1$ represents an alkanoyl group, and the hydroxy and $R^1$ substituents on the second formula are ortho to one another.

2. A process which comprises reacting a hydroxy-substituted coumarin of the formula

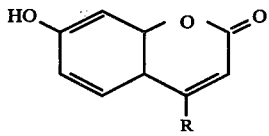

with an acylating agent containing an alkanoyl group, in the presence of a Friedel-Crafts catalyst and at a temperature of about 130° to 200° C., to produce a coumarin derivative of the formula

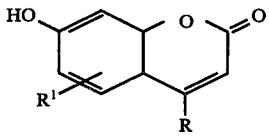

wherein in the formulas R represents an unsubstituted alkyl group, $R^1$ represents an alkanoyl group, and the hydroxy and $R^1$ substituents on the second formula are ortho to one another.

3. A process according to claim 2, wherein R represents an unsubstituted alkyl group having from 1 to 4 carbon atoms.

4. A process according to claim 3, wherein R represents methyl.

5. A process according to claim 2, wherein $R^1$ represents an alkanoyl group having from 1 to 6 carbon atoms.

6. A process according to claim 5, wherein $R^1$ represents acetyl.

7. A process according to claim 2, wherein the acylating agent employed is a compound of the formula $R^1COX$, wherein $R^1$ is as defined in claim 2, and X represents chlorine, bromine, hydroxy or —$OOCR^1$ where R is as defined hereinbefore.

8. A process according to claim 7, wherein the acylating agent employed is acetyl chloride, acetyl bromide, acetic acid or acetic anhydride.

9. A process according to claim 2, wherein the Friedel-Crafts catalyst employed is aluminum chloride, zinc chloride or ferric chloride.

* * * * *